(12) United States Patent
Haydock

(10) Patent No.: US 7,078,170 B2
(45) Date of Patent: Jul. 18, 2006

(54) REACTION MIXTURES FOR TARGET AMPLIFICATION OF NUCLEIC ACID WITH MUTANT RNA POLYMERASE

(75) Inventor: Paul V. Haydock, Shoreline, WA (US)

(73) Assignee: PBI Technology, Inc., Seattle, WA (US)

( * ) Notice: Subject to any disclaimer, the term of this patent is extended or adjusted under 35 U.S.C. 154(b) by 464 days.

(21) Appl. No.: 10/230,579

(22) Filed: Aug. 28, 2002

(65) Prior Publication Data

US 2003/0124515 A1  Jul. 3, 2003

Related U.S. Application Data

(62) Division of application No. 09/583,060, filed on May 30, 2000, now Pat. No. 6,531,300.

(60) Provisional application No. 60/137,267, filed on Jun. 2, 1999.

(51) Int. Cl.
*C12Q 1/68* (2006.01)
*C12P 19/34* (2006.01)

(52) U.S. Cl. .................. 435/6; 435/91.1; 435/91.2
(58) Field of Classification Search ............... 536/24.1; 435/6, 91.1, 91.2
See application file for complete search history.

(56) References Cited

U.S. PATENT DOCUMENTS

| | | | |
|---|---|---|---|
| 4,766,072 A | 8/1988 | Jendrisak et al. | |
| 5,037,745 A | 8/1991 | McAllister | |
| 5,399,491 A * | 3/1995 | Kacian et al. | 435/91.21 |
| 5,547,862 A | 8/1996 | Meador et al. | |
| 5,849,546 A * | 12/1998 | Sousa et al. | 435/91.5 |
| 5,849,547 A * | 12/1998 | Cleuziat et al. | 435/91.21 |

\* cited by examiner

*Primary Examiner*—Kenneth R. Horlick
(74) *Attorney, Agent, or Firm*—Townsend and Townsend and Crew LLP

(57) ABSTRACT

This invention provides a reaction mixture to amplify a nucleic acid. The mixture includes a double stranded DNA molecule with one or more primer recognition sites and a mutant RNA polymerase designed to transcribe deoxynucleotides.

5 Claims, 7 Drawing Sheets

SEQUENCE LISTING

```
<160> NUMBER OF SEQ ID NOS: 31

<210> SEQ ID NO 1
<211> LENGTH: 79
<212> TYPE: DNA
<213> ORGANISM: Artificial Sequence
<220> FEATURE:
<223> OTHER INFORMATION: Description of Artificial Sequence:synthetic
      oligonucleotide top strand with bacteriophage T7
      RNA polymerase promoter top strand, primers 1 and
      2 and tail sequence

<400> SEQUENCE: 1
aatttaatac gactcactat agggaatctc caacatccgc gaaatgcaaa caccaccatc    60
atccgatggc gaaaaaaaa                                                 79

<210> SEQ ID NO 2
<211> LENGTH: 96
<212> TYPE: DNA
<213> ORGANISM: Artificial Sequence
<220> FEATURE:
<223> OTHER INFORMATION: Description of Artificial Sequence:synthetic
      oligonucleotide bottom strand with bacteriophage
      T7 RNA polymerase promoter bottom strand, primers
      1 and 2 and bacteriophage T7 RNA polymerase
      promoter top strand
```

```
<400> SEQUENCE: 2
aatttaatac gactcactat agggacgcca tcggatgatg gtggtgtttg catttcgcgg      60
atgttggaga ttccctatag tgagtcgtat taaatt                               96

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:
      bacteriophage T7 RNA polymerase gene sequence

<400> SEQUENCE: 3
atgaacacga ttaacatcgc taagaac                                         27

<210> SEQ ID NO 4
<211> LENGTH: 54
<212> TYPE: DNA
<213> ORGANISM: Artificial Sequence
<220> FEATURE:
<223> OTHER INFORMATION: Description of Artificial Sequence:
      bacteriophage T7 RNA polymerase gene sequence containing RcaI
      site

<400> SEQUENCE: 4
tcgcagtgtg actaagcgtt cagtcatgac gctggcttac gggtccaaag agtt           54

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:
      bacteriophage T7 RNA polymerase gene sequence

<400> SEQUENCE: 5
ttagagtcgg acttcgcgtt cgcgtaa                                         27

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:
      bacteriophage T7 RNA polymerase gene sequence cleaved at RcaI
      site

<400> SEQUENCE: 6
tcgcagtgtg actaagcgtt cagt                                            24

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:
      bacteriophage T7 RNA polymerase mutant gene sequence cleaved at
      RcaI site

<400> SEQUENCE: 7
catgacgctg gcttacgggg ccaaagagtt                                      30

<210> SEQ ID NO 8
<211> LENGTH: 28
<212> TYPE: DNA
<213> ORGANISM: Artificial Sequence
```

```
<220> FEATURE:
<223> OTHER INFORMATION: Description of Artificial Sequence:
      bacteriophage T7 RNA polymerase mutant gene complementary
      sequence cleaved at RcaI site

<400> SEQUENCE: 8
catgactgaa cgcttagtca cactgcga                                      28

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:
      bacteriophage T7 RNA polymerase gene complementary sequence
      cleaved at RcaI site

<400> SEQUENCE: 9
aactctttgg ccccgtaagc cagcgt                                        26

<210> SEQ ID NO 10
<211> LENGTH: 54
<212> TYPE: DNA
<213> ORGANISM: Artificial Sequence
<220> FEATURE:
<223> OTHER INFORMATION: Description of Artificial Sequence:mutant
      bacteriophage T7 RNA polymerase gene sequence
      ligated at RcaI site

<400> SEQUENCE: 10
tcgcagtgtg actaagcgtt cagtcatgac gctggcttac ggggccaaag agtt         54

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence:
      phage-encoded RNA polymerase active site consensus sequence
<220> FEATURE:
<221> NAME/KEY: MOD_RES
<222> LOCATION: (2)...(8)
<223> OTHER INFORMATION: Xaa = any amino acid

<400> SEQUENCE: 11

Lys Xaa Xaa Xaa Xaa Xaa Xaa Xaa Tyr Gly Ser
  1               5                  10

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:
      bacteriophage T7 RNA polymerase consensus promoter sequence

<400> SEQUENCE: 12
aatttaatac gactcactat aggga                                         25

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:
      bacteriophage SP6 RNA polymerase promoter sequence
```

```
<400> SEQUENCE: 13
aattaggtga cactatagaa tag                                              23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:
      bacteriophage T3 RNA polymerase promoter sequence

<400> SEQUENCE: 14 aattaacccct cactaaaggg aag                                             23

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence:primer
      TSVN0011

<400> SEQUENCE: 15
cccccatatg aacacgatta acatcgctaa gaac                                  34

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence:primer
      TSVN0012

<400> SEQUENCE: 16 ccccccctgca gttacgcgaa cgcgaagtcc gactctaa                             38

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence:primer
      TSVN006

<400> SEQUENCE: 17
acacacacat catgactgaa cgcttagtca cactgcga                              38

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence:primer
      TSVN005

<400> SEQUENCE: 18
acacacacat catgacgctg gcttacgggg ccaaagagtt                            40

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence:primer
      TSVN005
```

```
<400> SEQUENCE: 19
tcatgacgct ggcttacggg gccaaagagt t                              31

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence:
      bacteriophage T7 RNA polymerase gene sequence around point
      where mutation introduced

<400> SEQUENCE: 20
actcgcagtg tgactaagcg ttcagtcatg acgctggctt acgggtccaa agagttcggc    60

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence:primer
      TSVN006

<400> SEQUENCE: 21
agcgtcacac tgattcgcaa gtcagtact                                 29

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence:bumper
      primer

<400> SEQUENCE: 22
ctcacagtgt acggacctaa ag                                        22

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:T7-39 primer

<400> SEQUENCE: 23
tacctaaagc ccagccaatc                                           20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:T7-215
      primer

<400> SEQUENCE: 24
ggctttaggt gttggcttta                                           20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:T7-500
      primer
```

```
<400> SEQUENCE: 25
tattcgccgt gtccctctcg                                               20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:T7-861
      primer

<400> SEQUENCE: 26
ccttgcgata cccttgagtt                                               20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:T7-1632
      primer

<400> SEQUENCE: 27
cgtagtgctt catcatttgc                                               20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:T7-3217
      primer

<400> SEQUENCE: 28
gttgaacggg atagcagcca                                               20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:T7-6535
      primer

<400> SEQUENCE: 29
ccagcgttat ccagagcctt                                               20

<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence:T7-39 primer
      with 5' consensus bacteriophage T7 RNA polymerase
      promoter added

<400> SEQUENCE: 30
aatttaatac gactcactat agggatacct aaagcccagc caatc                   45

<210> SEQ ID NO 31
<211> LENGTH: 45
<212> TYPE: DNA
<213> ORGANISM: Artificial Sequence
<220> FEATURE:
<223> OTHER INFORMATION: Description of Artificial Sequence:T7-215
      primer with 5' consensus bacteriophage T7 RNA polymerase
      promoter added
```

-continued

```
<400> SEQUENCE: 31
aatttaatac gactcactat agggaggctt taggtgttgg cttta                    45
```

REACTION MIXTURES FOR TARGET AMPLIFICATION OF NUCLEIC ACID WITH MUTANT RNA POLYMERASE

CROSS-REFERENCES TO RELATED APPLICATIONS

This is a divisional application of and claims the benefit of U.S. patent application Ser. No. 09/583,060, filed May 30, 2000, now U.S. Pat. No. 6,531,300, which claims the benefit of U.S. Provisional Application No. 60/137,267, filed Jun. 2, 1999, which application is incorporated herein by reference for all purposes.

STATEMENT AS TO RIGHTS TO INVENTIONS MADE UNDER FEDERALLY SPONSORED RESEARCH AND DEVELOPMENT

No Federal Rights

BACKGROUND OF THE INVENTION

Many forms of nucleic acid amplification reactions have been developed in recent years. The first method was the Polymerase Chain Reaction (PCR) which involved repeated cycles of heating to separate the DNA strands, primer annealing to the strands, and primer extension by a DNA polymerase. Product accumulation from the PCR reaction is exponential; that is, the amount of product doubles for every cycle of amplification. Therefore, the expected amount of product may be calculated by the formula $(Eff*2)^n$ where Eff is the efficiency of the primer annealing and primer extension reaction, and n is the number of cycles.

An alternative method for target amplification was developed called NASBA (Nucleic Acid Sequence Based Amplification). This method relies on the concerted action of three enzymatic activities, Reverse transcripts, RNaseH, and RNA Polymerase, to amplify an RNA target. Reverse transcriptases generally possess an endogenous RNase H activity, which can under the correct conditions, substitute for exogenously added RNase H activity. Primers are first designed which have an RNA polymerase site together with a target recognition sequence. Then, the primers are added to the target nucleic acid together with the three enzyme activities. First, primer binds followed by primer extension across the sequence of interest. The result is a double stranded RNA-DNA hybrid. The RNA portion of the hybrid is digested by the RNase H activity allowing binding of the other primer. The reverse transcriptase activity then extends this primer back across the sequence of interest finishing at the RNA polymerase binding sequence. The RNA polymerase activity then transcribes the sequence of interest making multiple single stranded RNA copies. These RNAs may bind more primers and the cycle continues. Because each transcription step yields 10–100 copies of RNA per copy of template, product accumulates rapidly and logarithmically.

Still, another method has been developed which is called SDA or Strand Displacement Amplification. This method utilizes four primer sequences with two primers binding on either end of the sequence of interest. It also requires a DNA polymerase and a restriction endonuclease (A restriction endonuclease binds to a specific sequence called its recognition site, and then cleaves the DNA a specific sequence). In the first step, nucleic acid strands are heat separated allowing the binding of the first primer pair. The inner primer contains a restriction enzyme site which is non-complementary to the target sequence, while the outer primer binds just upstream of the inner primer. DNA polymerase extends both primers, but extension from the outer primer displaces the newly synthesized inner strand yielding a single strand template for primer binding. Extension reactions are done in the presence of a nucleotide analog (alpha-thio-dATP such that the newly synthesized strands are fully substituted making them immune to cleavage by the restriction endonuclease. However, since the inner primers are not substituted, and the complement of the inner primer is substituted, the restriction enzyme will create a nick within the inner primer sequence by cutting only within the unsubstituted sequence. The nick can act as a priming site for DNA polymerase. In the process of extending the nick, the DNA strands are separated or displaced by the DNA polymerase creating single strand primers which can then bind inner primers for the next round of amplification. Accumulation of product for SDA is therefore exponential since every priming event doubles the amount of product.

Other amplification schemes have been devised, but they all require generating a single strand intermediate that allows primer binding for continued rounds of amplification. While the methods described above have been shown to work well, they do have some drawbacks. PCR requires the use of a thermocycler to obtain rounds of strand separation and primer extension. Furthermore, the process of heating and cooling can be slow resulting in a PCR reaction requiring a few hours to complete from start to finish. NASBA circumvents this issue by being run isothermally, that is at a single temperature. The products are single strand RNA which can be relatively unstable especially if an RNase activity, which are ubiquitous, is inadvertently introduced. RNA products are also generally chemically less stable. Furthermore, the length of the expected product dictates the efficiency of the amplification reaction. This is in part due to the reverse transcriptase activity which tend to be less processive than many DNA polymerases. NASBA reactions also require the addition of high concentrations of both ribonucleotides and deoxyribonucleotides increasing the cost of running a reaction. NASBA reactions are also run at lower temperatures leading to the production of spurious amplification products. In SDA, while the amplification products are DNA, the products are modified by the presence of the alpha-thio-dATP used to inhibit strand cleavage by the restriction endonuclease which may make further manipulation of the product difficult, especially in research applications.

There is a need for improved methods of nucleic amplification. This invention meets those needs.

SUMMARY OF THE INVENTION

This invention discloses a method for amplifying any nucleic acid sequence comprising of the steps (i) formation of an intermediate duplex [1] structure from any nucleic acid consisting of a complete double stranded RNA polymerase binding site, a region of sequence to be amplified, and a single stranded RNA polymerase binding site; (ii) binding of a mutant RNA polymerase which utilizes only dNTPS to the RNA polymerase binding site; (iii) transcribing the intermediate duplex to form the first primeness (+) single stranded amplification product [2]; (iv) binding of primer 2 [3] to the primeness (+) single stranded amplification product; (iv) extension of the primer sequence to yield amplification duplex 1 [4]; (v) transcription of amplification duplex 1 to produce the Primerless (−) Strand Single stranded amplification product [5]; (vi) bind primer 1 [6] to the Primerless (−) Strand Single stranded amplification product; (vii) extend Primer 1 by either the mutant RNA polymerase alone or with a second DNA polymerase activity to form amplification duplex 2 [7]; and (viii) transcription of amplification duplex 2 to produce the primeness (+) strand single stranded amplification product [2]. The cycle is continued until one or more of the necessary reaction components are exhausted.

More specifically, this invention is an isothermal amplification method of copying a nucleic acid sequence comprising the steps of:
a. providing an aqueous solution comprising
   i. a target nucleic acid for amplification said target comprising a double stranded DNA having a first 5' end which bears a phage-encoded RNA polymerase recognition site and a second 5' end which bears a phage-encoded RNA polymerase recognition sequence,
   ii. a first and second amplification primer each having a phage-encoded RNA polymerase recognition sequence wherein the first primer is complementary to the 5' end of the target sequence and the second primer is complementary to the antisense sequence of the 3' end of the target sequence,
   iii. phage-encoded RNA polymerase mutated to recognize and polymerize dNTP and,
   iv. an excess of dNTP;
b. repetitively allowing the polymerase to bind to its recognition site and to transcribe a first, short (−) copy strand of the target nucleic acid to yield a multiple copies of a primeness single (+) strand amplification product;
c. creating a first amplification duplex by allowing the second primer to bind to the primeness single (+) strand amplification products of step b and permitting the polymerase to (i) extend the primer to yield a polymerase primed (−) amplification product and (ii) extend the primeness (+) strand to include a polymerase primer complement sequence creating a polymerase recognition site;
d. repetitively allowing the polymerase to bind to its recognition site on the first amplification duplex and to transcribe multiple copies of a primeness single stranded (−) amplification product;
e. creating a second amplification duplex by allowing primer 1 to bind to the primeness single stranded (−) amplification products of step h and permitting the polymerase (i) to extend primer 1 to yield a polymerase primed (+) amplification product and (ii) to extend the primeness (−) strand to include a polymerase primer complement sequence creating a polymerase recognition site; and,
f. repetitively allowing the polymerase to bind to its recognition site on the second amplification duplex and to transcribe multiple copies of a primeness single stranded (+) amplification product.

The above-described method is optionally performed with a T7 RNA polymerase mutant such as Y639F and S641A. The target nucleic acid is optionally derived from a template nucleic acid having a subsequence as the target nucleic acid wherein the method further comprises the steps of: (i) placing the template nucleic acid in an aqueous solution comprising the first and second primers, the mutant phage polymerase and an excess of dNTP and (ii) permitting the polymerase and reactants to yield the target nucleic acid (intermediate duplex) comprising a double stranded DNA having a first 5' end which bears a phage-encoded RNA polymerase recognition site and a second 5' end which bears a phage-encoded RNA polymerase recognition sequence. The method can be performed using single stranded DNA as the target nucleic acid. Alternatively with the use of reverse transcriptase the target can be RNA.

In a related method this invention is a logarithmic, isothermal method of copying a nucleic acid sequence from a long strand of nucleic acid comprising the steps of:
a. providing an aqueous solution comprising:
   i. template nucleic acid having a target sequence for amplification,
   ii. a first and second amplification primer each having a phage-encoded RNA polymerase recognition sequence wherein the first primer is complementary to the 5' end of the target sequence and the second primer is complementary to the antisense sequence of the 3' end of the target sequence,
   iii. phage-encoded RNA polymerase mutated to recognize and polymerize dNTP and,
   iv. an excess of dNTP;
b. allowing the first primers to bind to the template nucleic acid at the 3' end of the target sequence;
c. creating target: long strand duplex by allowing the polymerase to extend the 3' end of the primer to create a first, long (+) strand complementary to the target subsequence;
d. displacing the template and the first, long (+) strand;
e. creating an intermediate duplex by allowing the second primer to bind to the long (+) strand at the 3' end of the target sequence and using polymerase to extend the second primer in a 3' direction to yield a first, short (−) copy strand bound to the long (+) strand;
f. repetitively allowing the polymerase to bind to its recognition site and to transcribe the first, short (−) copy strand of the intermediate duplex to yield a multiple copies of a primeness single (+) strand amplification product;
g. creating a first amplification duplex by allowing primer 2 to bind to the primeness single (+) strand amplification products of step f and permitting the polymerase to (i) extend the primer to yield a polymerase primed (−) amplification product and (ii) extend the primeness (+) strand to include a polymerase primer complement sequence creating a polymerase recognition site;
h. repetitively allowing the polymerase to bind to its recognition site on the first amplification duplex and to transcribe multiple copies of a primeness single stranded (−) amplification product;
i. creating a second amplification duplex by allowing primer 1 to bind to the primeness single stranded (−) amplification products of step h and permitting the polymerase (i) to extend primer 1 to yield a polymerase primed (+) amplification product and (ii) to extend the primeness (−) strand to include a polymerase primer complement sequence creating a polymerase recognition site; and,
j. repetitively allowing the polymerase to bind to its recognition site on the second amplification duplex and to transcribe multiple copies of a primeness single stranded (+) amplification product.

The methods described herein can comprise a reaction mixture further containing a bumper oligonucleotide which is: (i) able to hybridize to a DNA sequence about or adjacent to the 5' end of the first long strand and (ii) able to serve as polymerase primer which displaces the first long strand when extended towards the 3' end of the target nucleic acid.

This invention further comprises a novel composition comprising a double stranded DNA having a first and second end comprising a phage RNA polymerase recognition sequences on both the first and second ends wherein at least one end has a complementary sequence that forms a phage polymerase recognition site [1]. This is termed an intermediate duplex. The composition may also be a double stranded DNA having wherein both ends have phage polymerase recognition sites and the sites may be the same or different. The composition may optionally comprise a signature sequence for a specific genus or species of organism.

This invention also provides for a novel aqueous reaction mixture comprising: i. a target nucleic acid for amplification; ii. a first and second amplification primer [3,6] each having a phage-encoded RNA polymerase recognition sequence wherein the first primer is complementary to the 5' end of the target sequence and the second primer is complementary to the antisense sequence of the 3' end of the target sequence; iii. phage-encoded RNA polymerase mutated to recognize and polymerize dNTP; and, iv. an excess of dNTP. The reaction mixture may also comprise target nucleic acid which is a double stranded DNA having a first 5' end which bears a phage-encoded RNA polymerase recognition site and a second 5' end which bears a phage-encoded RNA polymerase recognition sequence.

This invention further provides for a kit for amplifying a target nucleic acid comprising a container containing a first primer having a sequence complementary to a 5' end of the target nucleic acid and a phage polymerase recognition sequence and a container containing a second primer having a sequence which is the anti-complement to the 3' end of the target nucleic acid and a phage polymerase recognition sequence. The kit may also have a mutant phage polymerase competent to incorporate dNTP into a template nucleic acid. The kit may also have a bumper oligonucleotide which is able to hybridize to a template DNA sequence where that sequence is about or immediately adjacent to the 3' base of the sequence to which one of the amplification primer binds.

The invention discloses methods to produce the intermediate duplex from any nucleic acid as well as a method based on the use of synthetic DNAs.

DETAILED DESCRIPTION

I. INTRODUCTION

Figure 1:
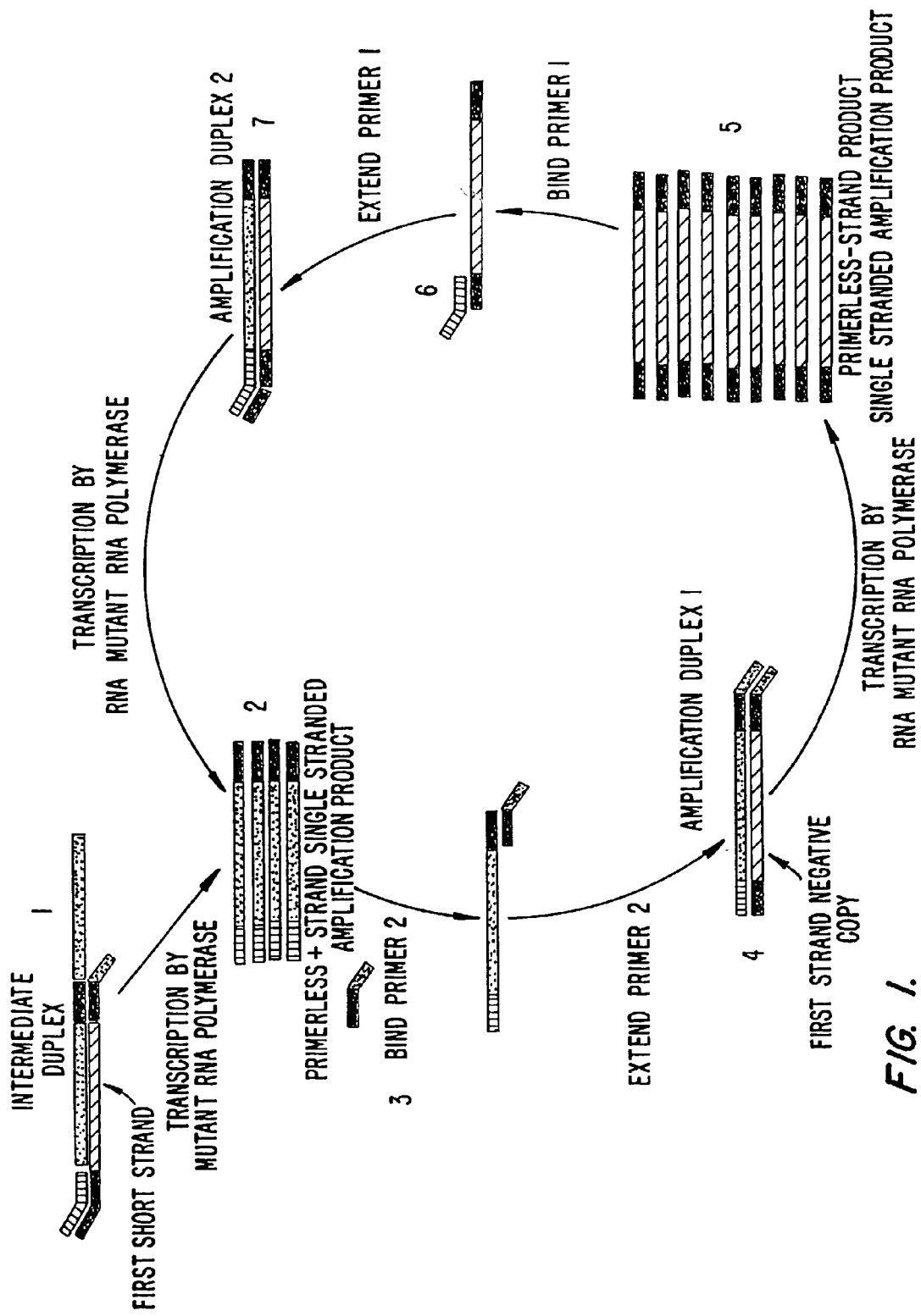
FIG. 1 is a schematic showing the cyclic nature of the amplification method described in this application. The cycle starts at the point of formation of the intermediate duplex [1].

This invention provides for a novel means for isothermally amplifying a target nucleic acid. The methods involves the use a unique family of phage-encoded polymerases which have properties which permit amplification of nucleic acids. The uses of amplification are identical to those used for conventional nucleic acid amplification processes such as the ligase chain reaction and polymerase chain reaction technologies. Such uses include medical diagnostics, microorganism identification, generation of multiple copies of nucleic acid for subsequent cloning and recombination work and forensics.

The amplification method of this invention is distinct from the amplification systems described above. These distinctions are also its advantages. Most notably, the amplification products are a mix of single and double stranded DNA. The single strand DNA is a particular advantage since detection of amplification may be done using hybridization with detector oligonucleotides without denaturing the entire reaction mix. The presence of double strand DNA is an advantage if products are to be further manipulated using standard molecular biology techniques, for example, if the amplification products are to cloned into a plasmid or phage. In addition, the products are unmodified and contain only deoxyribonucleotides found in the original target. Product accumulation is logarithmic, with each transcription reaction yielding 10–100 copies rapidly providing high yields of product. The reaction does not require a strand separation step, except at the start to get the reaction going. The reaction is isothermal and because some RNA polymerases are thermally stable to temperatures as high as 50 C., the reaction may be run at higher temperatures allowing increased specificity. The reaction is broadly applicable; i.e. it is not limited to any structural features of the template such as restriction enzyme sites. The reaction is not limited by the length of the amplification product, since many phage polymerases can transcribe large segments of DNA without falling off or pausing. Finally, the enzymes to be used in this reaction are highly stable, which will simplify the formulation of diagnostic kits.

II. DEFINITIONS

"Amplification duplex" refers to a double stranded DNA having a phage-encoded RNA polymerase recognition site at one end and primer complementary sequences at both ends. The amplification duplex is transcribed by the polymerase to produce multiple copies of its sense strand.

"Amplification primer" refers to a nucleic acid sequence which has a subsequence which complements either the 5' end or the 3' antisense end of a target nucleic acid and further comprises a phage-encoded RNA polymerase recognition sequence.

"First Amplification Primer" refers to a single stranded nucleic acid sequence that comprises from 5' to 3' a phage encoded RNA polymerase recognition sequence and a target recognition sequence complementary to the 3' end of the antisense strand of the target nucleic acid. "Second Amplification Primer" refers to a single stranded nucleic acid sequence that comprises from 5' to 3' a phage encoded RNA polymerase recognition sequence and a target recognition sequence complementary to the 3' end of the sense strand of the target nucleic acid.

"Double stranded DNA" refers to a duplex of two complementary DNA strands which by convention is drawn as a double line with a sense strand from 5' to 3' as the top line and an antisense strand from 3' to 5' as the bottom line.

"Isothermal amplification method" refers to a process of repetitively copying a target nucleic acid without using heat to separate the strands of any duplex formed during the process. This would not include the original target which may be heat separated before the amplification process begins.

"Phage-encoded RNA polymerase recognition site" refers to a double stranded nucleic acid sequence to which a phage-encoded RNA polymerase will bind and transcribe a copy of the antisense strand displacing the original antisense strand. The recognition site is not copied during this transcription process and results in a primeness copy of the original antisense strand.

"Phage-encoded RNA polymerase recognition sequence" refers to a sense nucleic acid sequence which is read from 5' to 3' and which is recognized by the polymerase as a "recognition site" when duplexed with the corresponding antisense sequence.

"Polymerase primed amplification product" refers to the strand of the amplification duplex strand which results from primer extension by the polymerase and consists of in 5' to 3' direction an amplification primer, the target nucleic acid and a antisense sequence for subsequent binding of a second amplification primer.

"Primerless single stranded amplification product" refers to products transcribed from either the intermediate duplex or the amplification duplexes.

"DNA:RNA" duplex refers to a heteroduplex where one strand is DNA and the other strand is RNA.

"Target nucleic acid" refers to a nucleic acid sequence or subsequence of a larger nucleic acid (template) that is the object of repetitive copying.

"Template nucleic acid" refers to a nucleic acid which has within it a target nucleic acid subsequence which will be amplified by the process of this invention.

"Transcribe" refers to the polymerase activity during which an amplification duplex is used by a polymerase as a template for creating copies of the sense strand.

III. PHAGE-ENCODED RNA POLYMERASES

RNA polymerases are a ubiquitous class of enzymes whose responsibility it is to copy DNA templates into RNA. RNA polymerases have been isolated from many sources both prokaryotic and eukaryotic. Some of the characteristics of these essential cellular enzymes are that they are generally larger multisubunit proteins. They are highly selective for ribonucleotides and cannot utilize deoxyribonucleotides. They are highly processive, and capable transcribing many kilobases of DNA without pausing or otherwise terminating. They produce multiple copies of RNA from each promoter.

While there are recognized terminator sites for phage polymerase transcription encoded in the phage DNA, routinely, these polymerases are used such that transcription stops by running-off the end of the DNA fragment being copied i.e. when the polymerase reaches the end of the end of the DNA fragment which it is copying, it dissociates from the template where it may be free to initiate new rounds of synthesis. This is sometimes referred to as run-off transcription.

The polymerases also have specific DNA sequences to which they bind which are referred to as promoter sequences. Promoter sequences are generally in the range of 10 to 40 base pairs in length and have a specific sequence for each specific RNA polymerase. Therefore, the RNA polymerase for $E.$ $coli$ will only bind to the specific promoter sequence of $E.$ $coli$. Minor variations in the promoter sequence affect the promoter strength i.e. how well the promoter is utilized by the RNA polymerase. Therefore, a strong promoter directs a large number of initiation reactions and therefore more RNA product while a weak promoter directs fewer initiations and therefore less RNA product.

Often times, when the minor promoter variants for a particular RNA polymerase are compared in both sequence and strength, a consensus promoter sequence can be derived which combines elements of all of the promoter sequences and leads to a "best" RNA polymerase promoter sequence.

In contrast to the cellular RNA polymerases described above, some RNA polymerases are encoded within phage DNAs such as the T phages which infect $E.$ $coli$. While the general characteristics are the same as the cellular RNA polymerases, the phage-encoded RNA polymerases are generally single subunit. The most common example of the phage-encoded RNA polymerases is that from bacteriophage T7. This enzyme has found considerable use in molecular biology as a means of preparing large amounts of specific RNAs form cloned fragments of PCR products. The phage-encoded polymerase of this invention bind to a specific promoter sequence. At this time, it is believed that all phage-encoded polymerases are suitable for use in this invention because they are all sequence specific. By sequence specific, we mean that they recognize a defined promoter sequence and can effect transcription from that sequence. A preferred group has a consensus sequence at their active site, which is K $AA_{1-7}$ Y G S (SEQ ID NO: 11) where $AA_{1-7}$ are independently selected and can be any seven amino acid residues.

When the RNA polymerase binds to its specific sequence, it then separates the DNA strands within the promoter sequence and initiates the transcription process. The RNA polymerase then moves down the DNA strand, separating the DNA strands and continuing to polymerize ribonucleotides in the exact sequence complementary to the DNA strand which it is copying. The DNA strands reanneal behind the polymerase and a single RNA strand is extruded from the polymerase. The RNA polymerase continues the copying process until either it reaches a termination site, or, until the polymerase reaches the end of the DNA strand and falls off. This ability to read long segments of DNA without falling off is called processivity, and a polymerase which can read very long segments of DNA and create very long RNA copies is referred to as highly processive. In general, RNA polymerases are highly processive making them particularly useful.

DNA polymerases used in other target amplification schemes are generally not sequence specific; they do not recognize and bind to a specific sequence in double stranded DNA. Rather, DNA polymerases require both a priming site and a template strand to copy. They will bind to the primer/template hybrids with virtually any sequence and begin to copy the template strand starting from the primer. Without an appropriate priming site, most DNA polymerases will be inactive, or may carry out non-specific nucleotide polymerization reactions. In DNA amplification reactions, the priming sites are contributed by the binding of the oligonucleotides of a specific sequence to the template strand. In contrast, many RNA polymerases do bind to specific sequences in double stranded DNAs. Notable among these phage-encoded polymerases are T7, SP6, and T3. All of these phage-encoded polymerases are commercially available, and have found great utility in synthesizing large amounts specific RNAs from cloned DNA fragments. These RNA polymerases have also been used in the NASBA technology by using promoter sequences specific for each polymerase on the primers.

IV. MUTANT RNA POLYMERASES

While the RNA polymerase from Bacteriophage T7 is described in detail in this invention, the invention is not limited to use of this polymerase. The mechanism of amplification is the same irregardless of the nature of the mutant RNA polymerase. This invention relies on the ability of a site specific enzyme capable of synthesizing DNA to mediate the amplification reaction. Therefore, it may be desirable to use other RNA polymerases if for example new RNA polymerases are discovered that are more thermostable, or if in the design of an assay, that a different promoter sequence is needed. In order to use other mutant RNA polymerases, it is necessary first to identify the mutation that lends the ability of the RNA polymerase to utilize deoxyribonucleotides. This may be done first by comparing the active site of the known S641A mutant of T7 RNA polymerase with the desired RNA polymerase. Since the active sites of several RNA polymerases is known, homologies and other similarities may be identified which will identify the amino acid residue that needs to be changed. Any method for site directed mufagenesis may then be used to introduce the desired mutation into the RNA polymerase. For example, it is known that the consensus sequence among active sites of several RNA polymerases is

K . . . Y G S (SEQ ID NO:11)

Another RNA polymerase, SP6 bears this exact active site sequence. It is predicted that changing the serine residue in this consensus sequence will allow for the construction of an SP6 polymerase with the ability to use deoxyribonucleotides rather than ribonucleotides, and yet maintain the promoter specificity of the natural SP6 RNA polymerase. When using a different RNA polymerase, the amplification reaction would be run in a similar manner to that described above except that the promoter sequence would match the specificity of the RNA polymerase being used. The use of different RNA polymerases may be an advantage in assays where it is desirable to amplify more than one gene. For example, if two genes are too amplified from one mixture, and both utilize the mutant T7 RNA polymerase binding site, then there may be competition between the two amplification reactions. This may be minimized by utilizing a second RNA polymerase with a different promoter specificity for the second gene.

V. AMPLIFICATION PRIMERS

Amplification primers will have the general structure:
    RNA Polymerase Binding Site—(Target Recognition Sequence)

The choice of amplification primers will be dictated on the target for amplification. However, the following criterion should be followed 1. Primers should be designed which will not cross-hydridize with each other taking into account the RNA polymerase binding site. 2. Primers should be chosen which have do not form secondary structures, again taking into account the RNA polymerase binding site. 3. Primer annealing temperatures should not be lower than within 5 C. above the reaction temperature 4. The primers should be in the range of 15 to 30 bases in length. However, it may be desirable to have shorter or longer recognition sequences 5. The ability of the primers to bind may be affected by secondary structure of the template strands. Secondary structure can prevent primer binding to the template and thus adversely affect the amplification yield. The easiest solution is to empirically scan the template strand with several primers whose target recognition sequences are displaced from each other by 2–5 bases. Usually regions can be found that effectively bind primers and which allow efficient amplification.

The structure of the RNA polymerase binding site will be dictated by the nature of the mutant RNA polymerase being used. The following table discloses the promoter sequences of three common RNA polymerases.

TABLE 1

Promoter Sequences for Various RNA Polymerases

| Polymerase | Promoter Sequence | |
|---|---|---|
| T7 | AATTTAATACGACTCACTATAGGGA | (SEQ ID NO:12) |
| SP6 | AATTAGGTGACACTATAGAATAG | (SEQ ID NO:13) |
| T3 | AATTAACCCTCACTAAAGGGAAG | (SEQ ID NO:14) |

Amplification primers are prepared synthetically by standard methods.

VI. MISCELLANEOUS COMPONENTS

Target nucleic acids may be obtained and prepared by any of a number of published procedures. This is not a critical step. Kits are commercially available to isolate and purify nucleic acids from a variety of sources. One reliable method for the preparation of bacterial nucleic acid involves first treating the bacteria sample with lysozyme (final concentration 100 ug/ml) for 15 minutes to 1 hour at room temperature in TEN buffer (10 mM Tris pH 7.5, 10 mM EDTA, 50 mM NaCl). An equal volume of TENS is then added (TEN buffer+2% SDS) together with Proteinase K (final concentration 500 ug/ml). The sample is heated to 50 C. for 1 hour or as long as overnight. The samples are then extracted at least once with phenol:chloroform:lsoamyl alcohol (50:49:1). Sodium acetate is then added to a final concentration of 0.3M from a 3M stock solution pH5.5. At least 2 volumes of 100% ethanol is then added and mixed well to precipitate the nucleic acid. The precipitate is spun at high speed in a microfuge for 5 minutes to pellet nucleic acids. The pellet is rinsed with 100% ethanol and dissolved in water.

dNTPs are prepared from commercially available stock solutions. For example, Sigma Corp. (St Louis) sells individual dNTPs at either 10 mM or 100 mM concentrations. The 10 mM stocks may be used directly in the amplification reactions. The 100 mM stocks must be diluted appropriately. It is convenient to mix each 100 mM dNTP stock together to create a 10 mM stock solution. For example, for each milliliter, mix 0.1 ml of each 100 mM dNTP stock. Then add 0.6 ml of 100 mM Tris pH 7.5. After mixing the components well, the final 10 mM dNTP stock is stored in 0.25 ml aliquots at −20 C. They are stable for at least a year when prepared in this manner. Alternatively, dry powder stocks of each dNTP may be purchased. This is considerably less expensive than purchasing premade stock solutions.

To prepare dNTP stock solutions from dry powders, 500 mg of each dNTP is dissolved in 4.2 ml of 50 mM Tris pH 7.5. The pH is then adjusted using a small quantity of 10N NaOH and using pH paper to monitor the pH. A 1/5,000 dilution is prepared of each dNTP and the absorbance is measured at the following wavelengths: dATP 259 nm, dCTP 271 nm, dGTP 253 nm, and TTP 260 nm. The concentrations of each dNTP stock is then calculated form the corresponding molar extinction coefficient: dATP E259=15400 l.mol-1.cm-1, dCTP E271=9100 l.mol-1.cm-1, dGTP E253=13700 l.mol-1.cm-1, TTP E260=7400 l.mol-1.cm-1. The concentrations are then adjusted to 100 mM using 50 mM Tris pH 7.5. A 10 mM stock solution may then be prepared as described above.

VII. REACTION CONDITIONS

The reaction conditions for the amplification scheme should be similar to the conditions needed for any standard transcription reaction. These conditions include 0.1M Tris-acetate pH 8.0 or within a range of pH 7.0 to pH 8.5, enough magnesium to balance out the dNTPs present in the reaction, which is in the range of 2 to 10 mM, dNTPs at a concentration of 200 uM to 1 mM.

A typical reaction may be performed as follows. A 5×Reaction Buffer is prepared which contains 0.2M Tris-acetate pH 8.0, 10 mM Mg acetate, 20 mM spermidine acetate, 0.25% Tween 20, 25 mM DTT. In some reactions manganese is added to a concentration of 10 mM in the reaction mix. Primers are prepared as a 100×stock solution at 100 uM. A 100 ul reaction mix is then prepared and contains: 20 ul 5×Reaction Buffer, 1 ul of each primer with or without the bumper oligonucleotide, 2 ul of dNTP mix, target nucleic acid, and water to 100 ul. The mixture is heated to 94 C. to denature the double stranded DNA target and then cooled to 42 C. Then 1 ul Klenow polymerase (exo$^-$) (five units) is added along with an optimized amount of the T7 mutant RNA polymerase. The reaction is then run at 42 C. for 15 minutes to 2 hours. Reaction products are then analyzed by gel electrophoresis or hybridization analysis. Products may be stored at −20 C.

VIII. DESCRIPTION OF THE TARGET AMPLIFICATION PROCEDURE

The cyclic amplification reaction is outlined in FIG. 1. The starting point of the reaction is called for purposes of description the intermediate duplex [1]. The intermediate is formed either synthetically, or in practical use by any of the means described below. The intermediate duplex has a complete double stranded copy of the RNA polymerase binding site followed by the sequence to be amplified. This is then followed by a second copy of the RNA polymerase binding site. Most often, this binding site will only be single stranded and non-complementary to the template strand. This means that this binding site is not functional.

In the first step of the amplification reaction, the mutant RNA polymerase will bind to the promoter sequence and in the presence of dNTPs and-magnesium, transcribe the intermediate duplex to create single strands labeled Primerless (+) Strand Single Stranded Amplification Product [2]. This product does not contain the RNA polymerase binding site since the RNA polymerase does not make a copy of the promoter. Also, since this is a transcription reaction, incorporation of primer is not directly necessary to produce these intermediate products. The single stranded products are then free to bind primer 2 [3]. Then, either the mutant RNA polymerase or a second added DNA polymerase will extend primer 2 across the amplified region. The primeness single stranded product will also be extended across the RNA polymerase promoter to which renders it active to bind the mutant RNA polymerase. This product is called Amplification Duplex 2 [4]. In the next step, the mutant RNA polymerase will transcribe the Amplification Duplex 2 to produce the Primerless (−) Strand Single Stranded Amplification Product [5]. This product is free to bind to primer 1 [6]. Then, primer 1 is extended across the target sequence. As before, the (−) Strand product is also extended across the RNA polymerase binding site to yield amplification duplex 2 [7]. Amplification Duplex 2 is transcribed by the mutant RNA polymerase to produce the Primerless (+) Single Stranded Amplification Product [2]. Further rounds of amplification will then occur following the same mechanism.

One important side reaction in this scheme is that the Primerless (+) and Primerless (−) Single Stranded Amplification Products [2,5] may anneal. This product will be unable to be further amplified since it does not have a functional RNA polymerase binding site. However, due to the see-saw mechanism of the amplification i.e. transcription of one strand followed by transcription of the other, the concentrations of the (+) and (−) strands will always be out of balance so that some single strand product will always be present to continue the amplification cycle. Further, since there will be an excess of primers present, hybridization to primer will be faster and favored over hybridization between strands.

Figure 2:
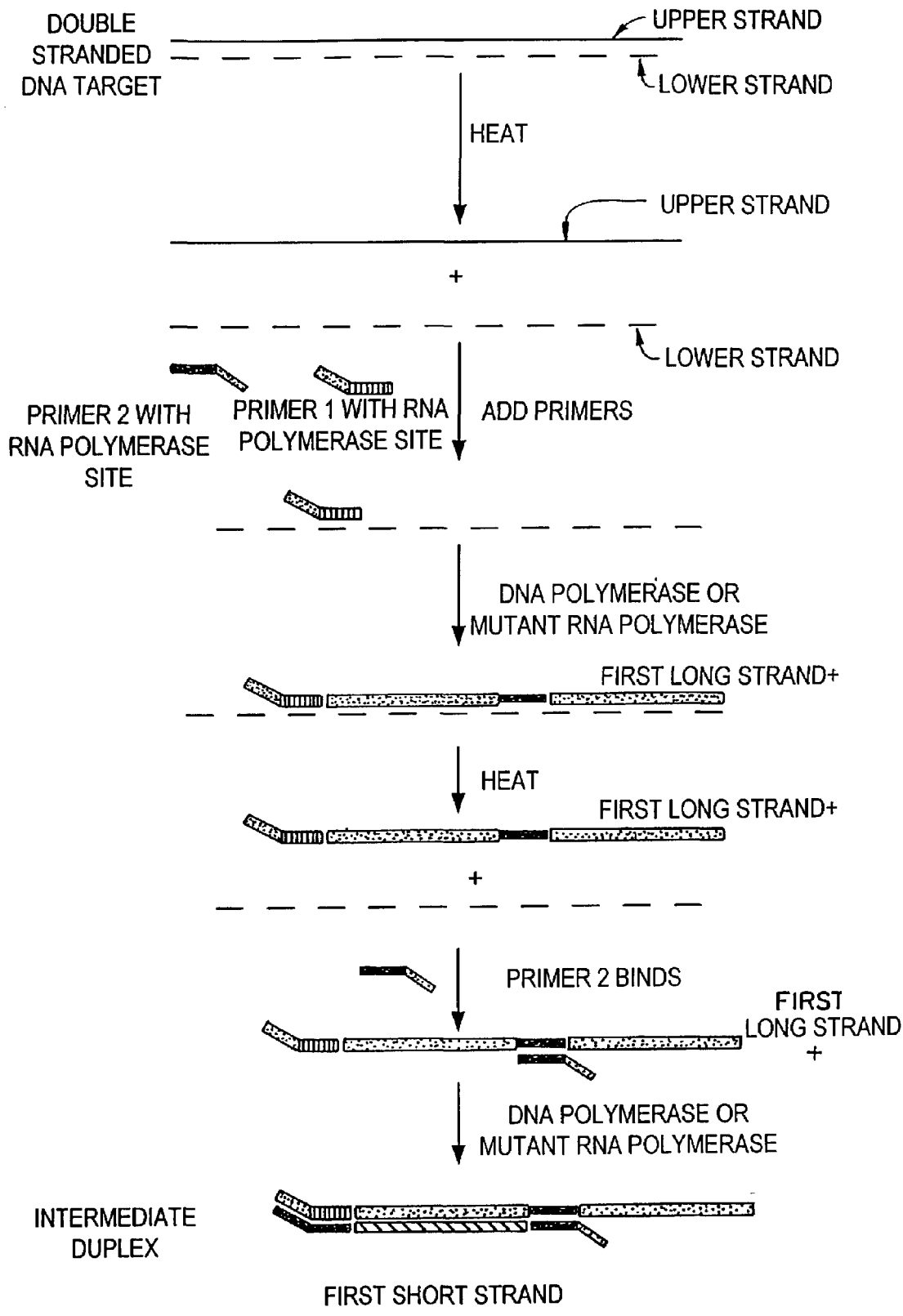
FIG. 2 shows the formation of the intermediate duplex starting with a double stranded DNA target. This scheme utilizes two heating steps to denature the double strand DNA target, and dissociating the first long strand (+) from the template.

The intermediate duplex [1] can be created by several methods. FIG. 2 shows in detail the production of the intermediate duplex from a double stranded DNA target. In the first step, the double stranded target is denatured by heating the sample above the melting temperature of the duplex. Primers are then added to the mix followed by cooling of the mixture to allow annealing of the primers. The next step is extension of the bound primer by either the mutant RNA polymerase activity, or another DNA polymerase such as Klenow polymerase, DNA polymerase I, T7 DNA polymerase, Taq Polymerase, or any other DNA polymerase activity. After the extension reaction, the newly synthesized strand is separated from the template strand by heating. This is followed by annealing of the second primer and extension of the bound primer to form the intermediate duplex.

IX. SYNTHETIC PREPARATION OF INTERMEDIATE DUPLEX

Figure 6:
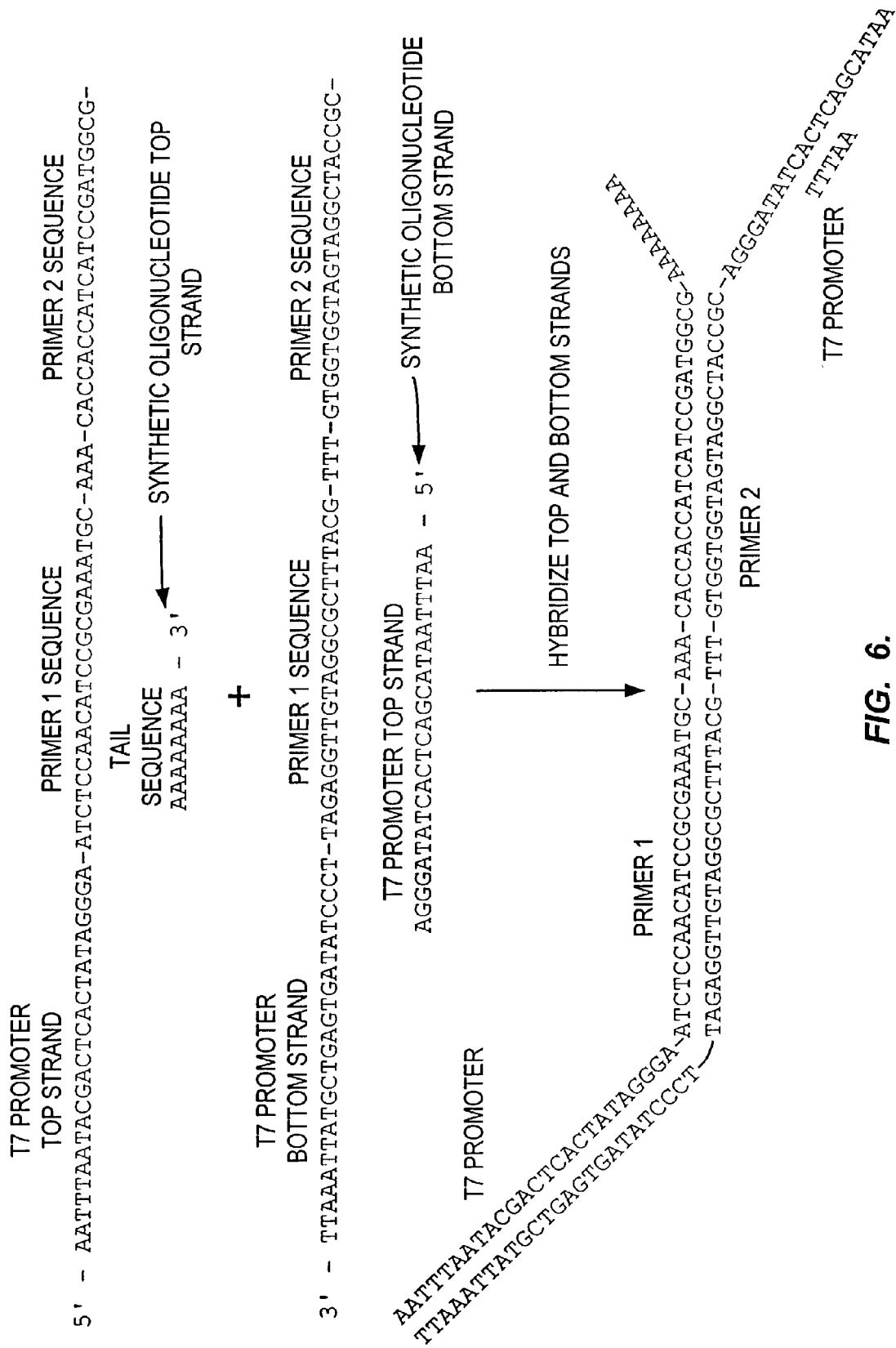
FIG. 6 shows how and intermediate duplex can be formed from two long synthetic oligonucleotides (SEQ ID NOS: 1 and 2). The characteristics of the intermediate duplex are the presence of the complete RNA polymerase binding site and a single stranded RNA polymerase binding site with a non-complementary opposing strand.

The key features of the intermediate duplex are that it has a complete double strand copy of the RNA polymerase site at one end, and two non-complementary single stranded tails at the opposite end. Thus, there is only one polymerase recognition site. It is possible to prepare this structure synthetically since DNA strands as long as 100 bases can be synthesized relatively efficiently. The following is an example for the preparation of an intermediate duplex using the T7 RNA polymerase promoter (See FIG. 6). As shown in FIG. 6, two DNA strands are synthesized, an upper and lower strand. The upper strand has a sense copy of the T7 RNA Polymerase promoter, a sense copy of the first primer sequence, a short bridge sequence (a string of 3 A's in the figure), an antisense copy of the second primer sequence, and a short tail sequence. The lower strand has an antisense copy of the T7 promoter sequence, and antisense copy of the first primer, a short bridge complement, a sense copy of the second primer sequence, and a sense copy of the T7 RNA polymerase binding site.

It is also possible to use an intermediate duplex having RNA polymerase recognition sites at both ends. Such a DNA would result from attaching RNA polymerase primers to both ends of a DNA sequence cut from a larger DNA using endonuclease restriction enzymes.

Note that since there is a sense and antisense copy of the RNA polymerase binding site on the lower synthetic strand, this strand may form hairpin loops between these two complementary sequences. It can also form longer polymers of the lower strand. Formation of the hairpin structure follows zero order kinetics, that is, it is independent of the concentration of the lower strand oligonucleotide. However, the formation of a perfect pair between the upper and lower strands should be thermally more stable than the hairpin structure. Therefore, upper and lower strand will be mixed in approximately equimolar amounts. The mixture will be heated to 95 C. to render each oligonucleotide single stranded. The mixture will then be slow cooled over several hours to allow hybrids to form. The mixture will then be subjected to reverse phase HPLC to distinguish the products of the hybridization reaction which will include excess unhybridized upper and lowers strands, and the hybrid which is the synthetic intermediate duplex.

X. VARIATIONS ON THE PROCEDURE.

Figure 3:
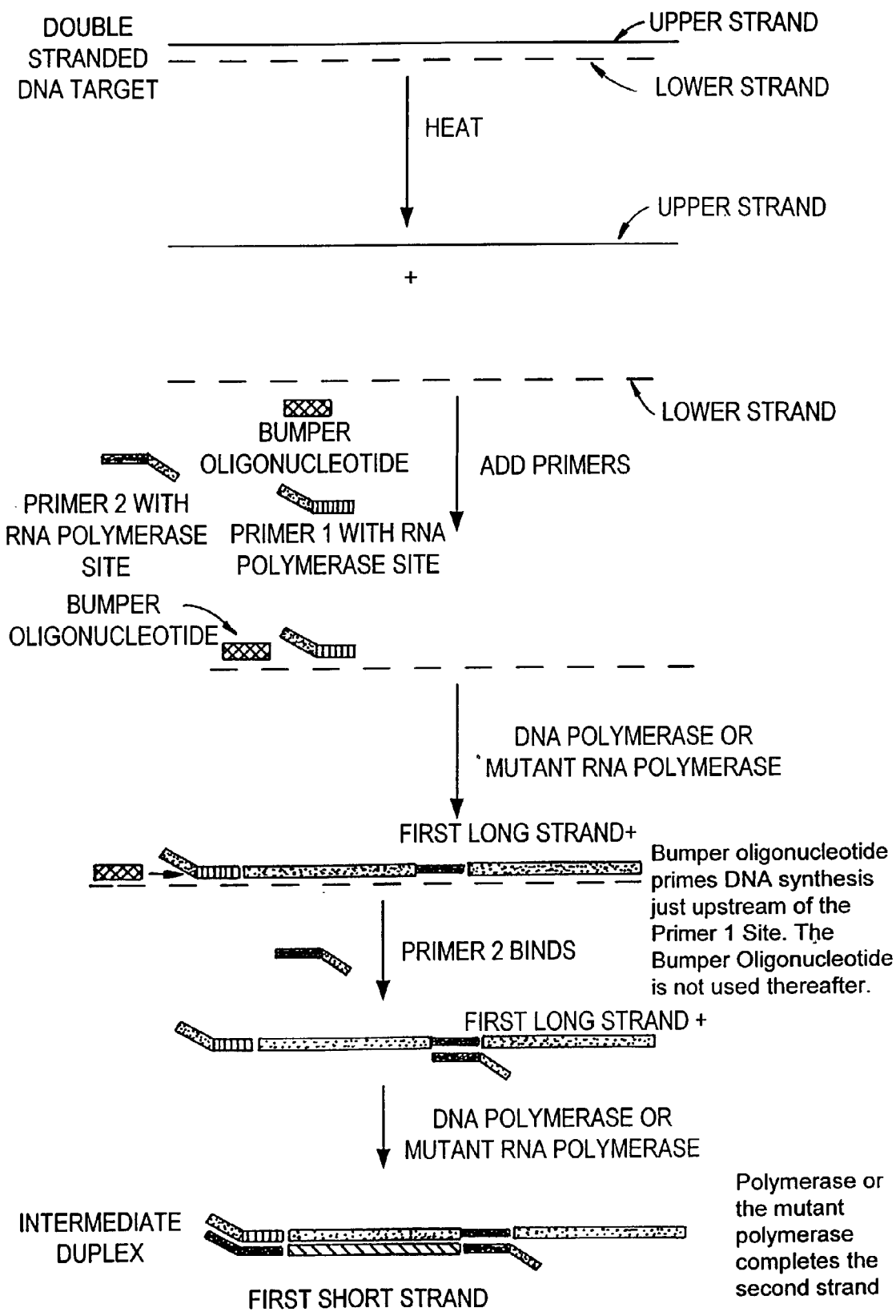
FIG. 3 shows the same basic scheme, but utilizing the bumper oligonucleotide to dissociate the first long strand (+) from the template strand.

FIG. 3 shows how the intermediate duplex would be formed using a third oligonucleotide called the "bumper" oligonucleotide. The bumper oligonucleotide binds to a sequence just upstream of either primer 1 or primer 2. In this method, the double stranded DNA target is heated to separate the strands allowing binding of primer 1 and the bumper oligonucleotide. The DNA polymerase activity will extend both Primer 1 and the bumper oligonucleotide. However, extension of the bumper oligonucleotide will result in displacement of the newly synthesized primer 1 extended strand. This allows binding of primer 2 to the first long strand (+) and extension of primer 2 to form the intermediate duplex.

Figure 4:
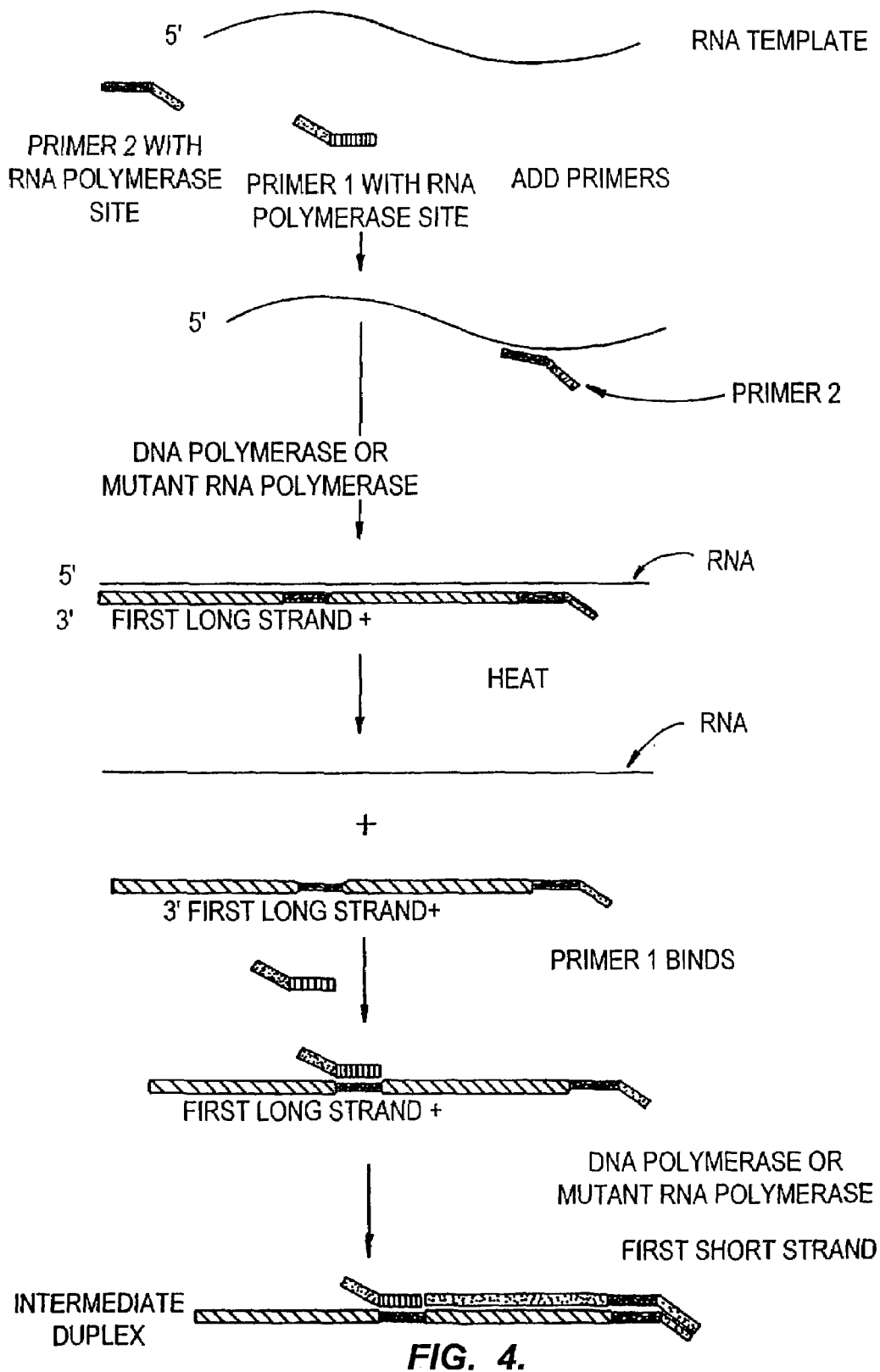
FIG. 4 shows how the intermediate duplex would be formed from an RNA template and utilizing a heating step to dissociate the first long strand (+) from the template RNA after the reverse transcription step.
Figure 5:
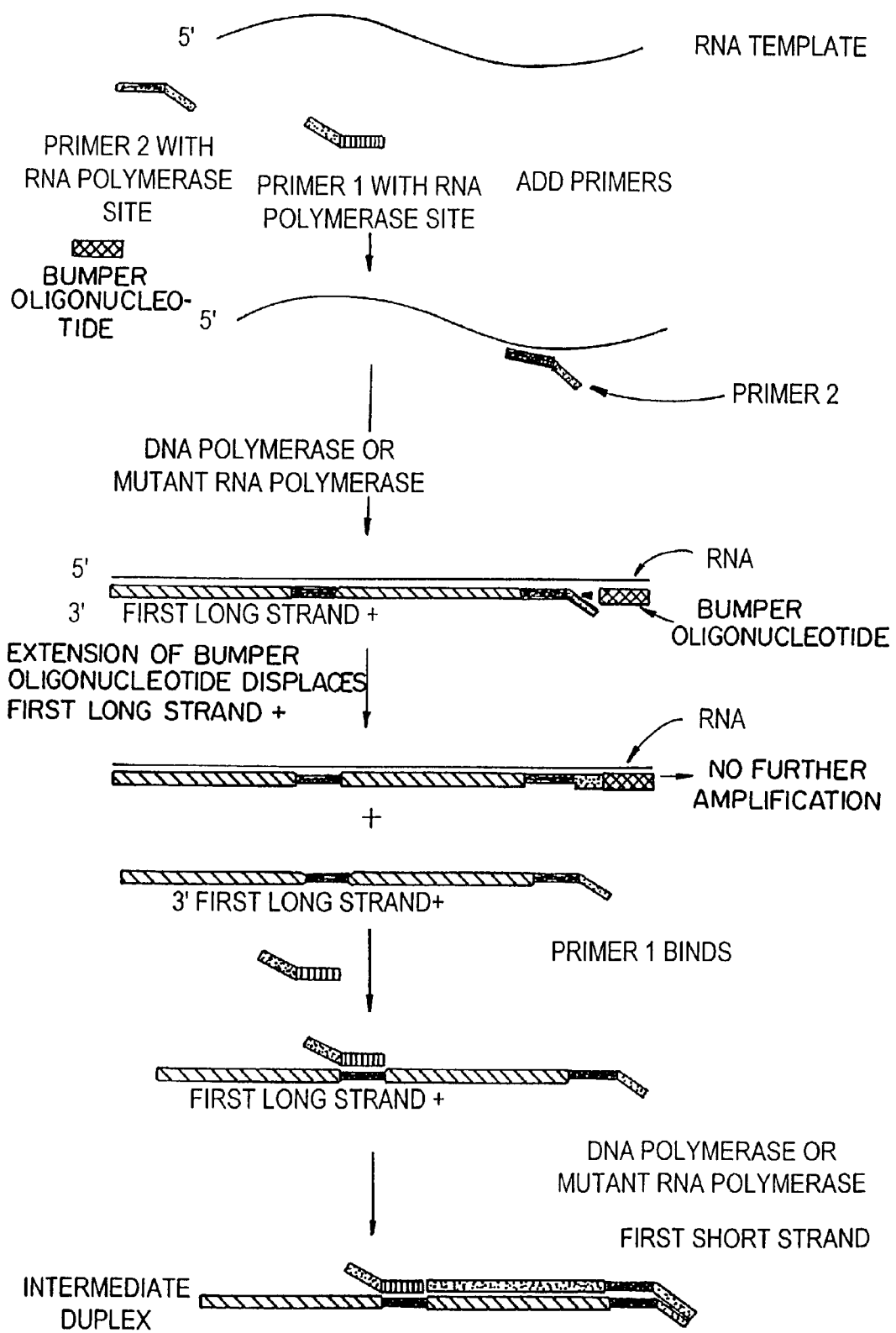
FIG. 5 shows how the intermediate duplex would be formed from an RNA strand utilizing the bumper oligonucleotide to dissociate the first long strand (+) from the RNA strand after the reverse transcription step.

The amplification method can also be used to amplify RNA sequences (See FIG. 4 and FIG. 5). The first step of the RNA amplification reaction must be the conversion or reverse transcription of the RNA template to a DNA copy. Mutant RNA polymerases may also have an associated reverse transcriptase activity. However, it may be preferable or more efficient to perform the reverse transcription reaction independently of the amplification reaction. The reverse transcription reaction contains 50 mM Tris-Cl pH8.8, 6 mM MgCl2, 10 mM DTT, and dNTPs at 1 mM each in a total volume of 20 ul. The RNA template is added along with the Reverse Transcriptase (2 units AMV RT, 200 units MMLV RT). Incubate at 42 C. for 30 minutes to 1 hour. The reverse transcription reaction is heated to 95 C. for 2 minutes to denature the completed strands and then diluted into the amplification reaction buffer as described above (FIG. 4). Alternatively, a bumper oligonucleotide may be utilized as described above (FIG. 5). In this case, the ability of the mutant RNA polymerase or the reverse transcriptase activity to displace the newly synthesized strand must first be determined. If the bumper oligonucleotide can be used, then the amplification reaction from RNA will be completely isothermal since no denaturation step is necessary.

XI. KITS

The practice of this invention may be made more convenient by the using a kit format. The kit may contain all of the components necessary to practice the invention together with detailed instructions. For example, a kit may contain a vial of the mutant RNA polymerase, a vial of a second DNA polymerase which may increase the efficiency of the amplification reaction, a dNTP mix, an optimized reaction buffer, control primers and template so the user may determine the efficiency of amplification. The user would supply specific primers for the application and template nucleic acids. A detailed set of instructions would include selection criteria for the preparation of primers, suggestions for template preparation, and detailed instructions on how to practice the invention.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

1. Mutation of a Specific Polymerase

Figure 7:
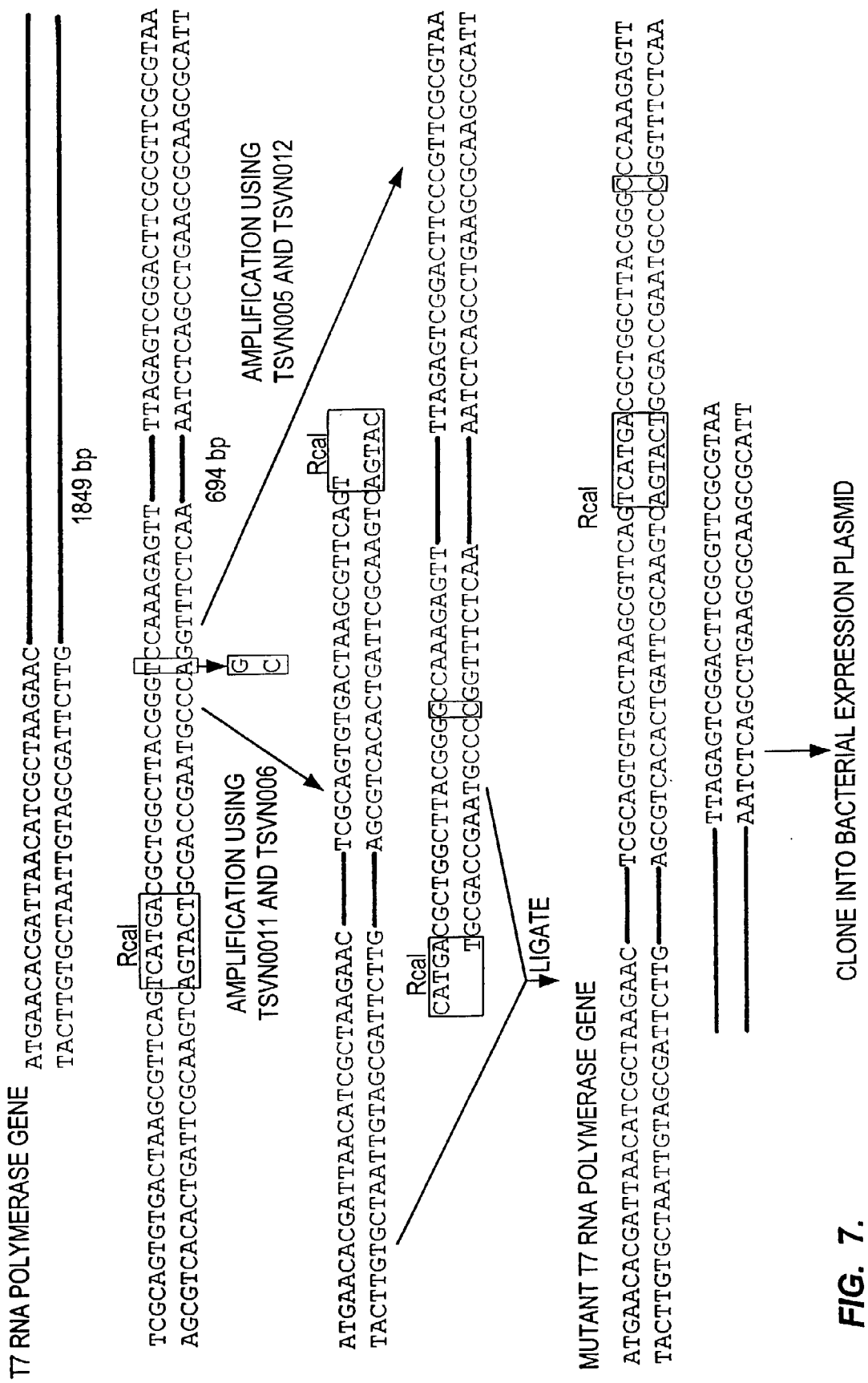
FIG. 7 shows one scheme for the introduction of a single base mutation into T7 RNA polymerase that results in a mutant RNA polymerase that utilizes only dNTPs and not rNTPs. T7 RNA polymerase gene sequences=SEQ 3ID NOS:3–5; sequences cleaved by Rcal=SEQ ID NOS:6–9; ligated mutant T7 RNA polymerase gene sequences=SEQ ID NOS:3, 10 and 5, respectively.

There are a number of published procedures for si+e directed mutagenesis, and some manufacturers offer complete kits for performing site directed mutagenesis. The procedure described below is designed to introduce the S641A mutation into coliphage T7 RNA polymerase using the Polymerase Chain Reaction (See FIG. 7). The method may be used for other RNA polymerases.

Purified T7 phage DNA is first obtained from Sigma Corp. PCR primers must be designed which will introduce the S641 mutation into the RNA polymerase gene. To do this, the GenBank database was searched for published RNA polymerase sequences (Accession Number M38308). Then, primers are designed coding for the 5' end and 3' end of the gene. These primers include restriction enzyme sites which will make cloning of the gene into a bacterial expression vector much easier.

TABLE 2

Primer Design for Mutant T7 RNA Polymerase Cloning

| Primer | Description | Sequence |
| --- | --- | --- |
| TSVN0011 | 5' end of coding sequence | CCCCCATATGAACACGATTAACATCGCTAAGAAC (SEQ ID NO:15) |

TABLE 2-continued

Primer Design for Mutant T7 RNA Polymerase Cloning

| Primer | Description | Sequence |
|---|---|---|
| TSVN0012 | 3' end of coding sequence | CCCCCCTGCAGTTACGCGAACGCGAAGTCCGACTCTAA (SEQ ID NO:16) |
| TSVN006 | 3' internal sequence, just upstream of the mutation | ACACACACATCATGACTGAACGCTTAGTCACACTGCGA (SEQ ID NO:17) |
| TSVN005 | 5' Internal Primer, including the mutation | ACACACACATCATGACGCTGGCTTACGGGGCCAAAGAGTT (SEQ ID NO:18) |

The sequence of the T7 RNA polymerase gene around the point where the mutation must be made is shown below (SEQ ID NOS: 19–21):

TSVN005

TCATGACGCTGGCTTACGGG(G)CCAAAGAGTT

ACTCGCAGTGTGACTAAGCGTTCAGTCATGACGCTGGCTTACGGG(T)CCAAAGAGTTCGGC

TGAGCGTCACACTGATTCGCAAGTCAGTACTGCGACCGAATGCCC(A)GGTTTCTCAAGCCG

AGCGTCACACTGATTCGCAAGTCAGTAGT

TSVN006

The nucleotide residue that must be changed is contained within the parentheses. It entails changing the T residue at position 1921 of the coding sequence to a G thereby changing the corresponding amino acid from an serine to an alanine. The gene sequence shows the presence of a unique Rca 1 restriction enzyme cleavage site (TCATGA) just upstream of the desired amino acid change. This site may be used as a focal point for introducing the S641A mutation. First, T7 DNA is amplified using TSVN011 and TSVN006 which amplifies the 5' segment of the gene. T7 is also separately amplified using primers TSVN005 and TSVN012 which produces the 3' end of the gene with the mutation in the correct place. Since PCR yields products which are blunt-ended, the next step would be digest the products with Rcal and Ndel for the 5' segment, and Rcal and Pstl for the 3' segment. Small fragments at the ends that result from the digestion are purified away by ultrafiltration.

A plasmid vector is chosen which will be used to express the mutant T7 gene in bacteria. The vector chosen for this purpose is pLEX which can be commercially obtained from Invitrogen Corp. This vector has the very strong lambda leftward promoter located just upstream of an Ndel site which also overlaps the start codon of the gene. The lambda leftward promoter is controlled by the lambda cI repressor which has been inserted into the genome of the host strain of *E. coli* for this plasmid which is GI724. The cI gene product is under control of the trp promoter which is itself regulated by the trp repressor protein. When the cells are grown in the absence of tryptophan, the trp repressor protein does not bind to the trp promoter so that the cI repressor protein is expressed which can bind to the lambda leftward promoter and inhibits expression of the cloned gene. When the cells are grown in the presence of trytophan, the trp repressor protein binds to the trp promoter thereby inhibiting expression of the cI protein. Without cI protein, the lambda leftward promoter is is fully turned on and the cloned gene is expressed to very high levels.

pLEX is cut to completion with Ndel and Pstl releasing a small fragment which is removed by ultrafiltration. The 5' and 3' segments along with the digested pLEX are combined and ligated overnight. A portion of the ligation mix is used to transform competent GI724 cells. Ampicillin resistant colonies are screened for the presence of the cloned gene by PCR using TSVN011 and TSVN012 as primers. Examination of the mutated gene indicates that the mutation creates a site for the restriction enzyme HaeIII. Digestion of the wild type gene with HaeIII leads to 4 fragments of 1415, 807, 318, and 112 base pairs. For the mutant gene, the mutation creates a HaeIII site in the 1415 base pair fragment leading to two fragments of 731 and 684 base pairs respectively. Therefore, the absence of the 1415 base pair fragment will indicate the successful cloning of the mutant T7 RNA polymerase gene. A single isolate, hereafter called the "Overproducing Strain" is saved and used for preparation of the protein.

2. Purification of Mutant RNA Polymerase

Next, the mutant RNA Polymerase must be purified from the overproducing strain. Purification of T7 RNA polymerase has been described in the scientific literature, and a modified and simplified procedure is as follows. Medium for growing the cells must have little or no tryptophan to minimize expression of the cloned gene. First, a saturated overnight culture is prepared in ACH/M9 medium (minimal medium). The saturated overnight culture is diluted 1:10 into 2 liter flasks, each of which contains 1 liter of ACH/M9 medium with 100 ug/ml ampicillin. The flasks are shaken and maintained at 30 C. for 4 hours at which time tryptophan is added to 100 ug/ml. Temperature is maintained at 30 C. and the cells are shaken for an additional 2 hours. Cells are harvested by centrifugation and stored at −70 C. Total yield of cells is about 2.5 g per liter of medium.

T7 RNA polymerase is readily degraded by a protease which is present in the cell membrane called OmpT protease. This protease has the properties that it is expressed in many strains of E. coli at higher temperatures, and that it is released from the cell membrane using detergent lysis of the cells. Therefore, to minimize omp T proteolysis, the cells are not grown at any point at 37 C., nor is there any detergent used in the lysis procedure.

The cell pellet was frozen in 20 ml lysis buffer. Purification is initiated by thawing the cells at room temperature. The lysis buffer is made of 25 ml of Buffer C (20 mM Tris-Cl, pH 8.0, 1 mMEDTA, 1 mM DTT, 5% glycerol) which is added together with 20 mg of lysozyme, 200 ul phenylmethylsulfonyl chloride (20 mg/ml in isopropanol), and 100 ul leupeptin (Sigma; 5 mg/ml in water). Mix the solution well and incubate at 4 C. for 45 minutes. Cells are lysed by repreated freeze/thaw cycles. The cell suspension is mixed and frozen at −80 C. for 30 minutes. The suspension is then thawed and refrozen at −80 C. Then, thaw the suspension at room temperature resulting in a highly viscous suspension.

Place the suspension in a blender and blend in several short bursts until the suspension is uniformly liquified. Spin the suspension at 5400 RPM for 20 minutes to pellet the cell debris. Dilute the suspension to 45 ml and add 5 ml 10% polymin P dropwise. After stirring for 20 minutes, pellet the precipitated nucleic acids for 20 minutes at 5400 RPM. To the supernatant, add 35 g solid ammonium sulfate per 100 ml of lysate. Stir the suspension at 4 C. to precipitate the protein at 4 C. for at least 20 minutes or overnight. Spin out the precipitate at 12.5 K for 20 minutes. Decant the supernatant and drain the pellets well. Add Buffer C to dissolve the pellets, and spin out any insoluble material at 12.5 K for 20 minutes.

Check the conductivity of the suspension and adjust with Buffer C so that it is close to that of Buffer C+50 mM NaCl. Load the sample onto a 20 ml column of SP Sepharose. Wash the column with Buffer C+50 mM NaCl until the OD280 comes down to baseline. Elute the bound protein with Buffer C+0.2 M NaCl. One major protein peak containing the mutant RNA polymerase is eluted. Read the OD280 of each fraction and combine the peak fractions.

Load these directly onto a 5 ml Cibacron Blue column equilibrated in Buffer C. Wash the column with Buffer C+0.5M NaCl which removes some contaminating proteins while the mutant polymerase remains tightly bound. Elute the mutant polymerase with Buffer C+2 M NaCl. Collect 2 ml fractions and read the A280 of each fraction. Pool the major peak fraction and dialyze into Buffer C+100 mM NaCl+50% glycerol. The concentration of the enzyme is deteremined from it's absorbace at 280 nm using a molar extinction coefficient of $1.4 \times 10^{-5}$ M-1 cm-1. Store in aliquots at −20C.

To assess the activity of the purified protein, a simple transcription assay may be run as follows. Prepare a 5×transcription buffer by mixing 200 ul of 1 M TrisAcetate pH 8.0, 25 ul of 1M DTT, 1-ul of 0.5M EDTA, 40 ul of 1M Spermidine, 25 ul of 25% Tween, and 0.7 ml of water. The reaction is set up by mixing 2 ul of 5×buffer, 4 ul of 10 mM dNTPs or rNTPs, either 1 ul of 150 mM MnCl2 or 1 ul of 100 mM MgCl2, 100–500 ng of template containing the T7 promoter, and water to 9 ul. Then, 1 ul of diluted polymerase is added and the reaction incubated for 1–2 hours. The products are run on a 2% agarose gel in 1×TAE at 75V–100V until done. The products are visualized using ethidium bromide.

3. Preparation of the Primers for Amplification of T7 DNA

To demonstrate the effectiveness of the Mutant RNA polymerase amplification system, a set of primers were designed utilizing T7 DNA as a template (Genbank Accession Number V01127).

TABLE 3

Amplification Primers for Various Segments of the Bacteriophage T7 Genome

| Designator | Coordinate | Sequence | Tm | Length of Product |
|---|---|---|---|---|
| Bumper | 2 | CTCACAGTGTACGGACCTAAAG (SEQ ID NO:22) | 50.6 | — |
| T7-39 | 39 | TACCTAAAGCCCAGCCAATC (SEQ ID NO:23) | 53.2 | — |
| T7-215 | 215 | GGCTTTAGGTGTTGGCTTTA (SEQ ID NO:24) | 51.2 | 195 |
| T7-500 | 500 | TATTCGCCGTGTCCCTCTCG (SEQ ID NO:25) | 59.5 | 480 |
| T7-861 | 861 | CCTTGCGATACCCTTGAGTT (SEQ ID NO:26) | 53.1 | 841 |
| T7-1632 | 1632 | CGTAGTGCTTCATCATTTGC (SEQ ID NO:27) | 50.6 | 1511 |
| T7-3217 | 3217 | GTTGAACGGGATAGCAGCCA (SEQ ID NO:28) | 57.2 | 3197 |
| T7-6535 | 6535 | CCAGCGTTATCCAGAGCCTT (SEQ ID NO:29) | 55.6 | 6515 |

Primer T7-39 will be the common primer at the 5' end of the amplified region. All other primers will be at the 3' end of the amplified region. Primers will have the consensus T7 RNA Polymerase Promoter Added to their 5' ends: AATTTAATACGACTCAC-TATAGGGA (SEQ ID NO:12)

In this table, primer T7-39 will be used as the primer at the 5' end of the amplified segment for all of the other primers. A bumper oligonucleotide is also included which binds just upstream of the T7-39 binding site, and provides an initiation point for displacing the upper strand after the initial DNA synthesis step. The 3' primers form a set that increases the expected size of the amplification units. This was done to demonstrate that since the RNA polymerase is highly processive, that the amplification reaction can be used to amplify increasingly large segments of DNA.

4. Selective Amplification of Portions of the T7 Genome

A 5×Reaction Buffer contains 0.2M Tris-acetate pH8.0, 20 mM spermidine acetate, 0.25% Tween 20 and 25 mM dithiothreotol (DTT). Primers are prepared as a 100×stock solution at 100 uM. The primers have the following structures:

T7-39 (SEQ ID NO:30)
AATTTAATACGACTCACTATAGGGA-TACCTAAAGCCCAGCCAATC

T7-215 (SEQ ID NO:31)
AATTTAATACGACTCACTATAGGGA-GGCTTTAGGTGTTGGCTTTA

The bumper oligonucleotide will be prepared as a 100 uM stock. The template DNA is commercially available from Sigma Corp (St. Louis). DNA supplied at 0.5 mg/ml. Therefore, 1 ul will supply 0.5 ug to the amplification reactions. A 100 ul reaction mix is then prepared and contains: 20 ul 5×Reaction Buffer, 1 ul of each primer, 1 ul of the bumper oligonucleotide, 2 ul of dNTP mix, 1 ul target nucleic acid, and 75 ul H$_2$O. A reaction is also prepared which has no template added. The mixtures are heated to 94 C. to denature the double stranded DNA target and then cooled to 42 C. Between 1 and 100 units of the T7 mutant RNA polymerase is added together with between 1 and 10 units of the Klenow fragment of DNA Polymerase I. In certain reactions, the efficiency of the amplification will be measured without the addition of the second DNA polymerase activity. The reaction is then run at 42 C. for 15 minutes to 2 hours. Reaction products are then loaded onto a 1.5% agarose gel followed by electrophoresis at 100V. Products are visualized by ethidium bromide staining.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following example is provided by way of illustration only and not by way of limitation. Those of skill will readily recognize a variety of noncritical parameters which could be changed or modified to yield essentially similar results.

Example 1

Isothermal Amplification Using a Mutant RNA Polymerase

A 5×buffer was prepared which consisted of 0.2 ml of 1M Tris pH8.3, varying amounts of 1M MgCl$_2$, 0.01 ml 1M DTT, 0.01 ml of 0.5M Spermidine, 0.04 ml of 2.5M KCl, and water to 1 ml. The reaction mixture contains 4 ul of 5×buffer, 2 ul of 10 mM dNTPS, 2 ul of a primer stock that contains 1 uM each of T7-39 and T7-215, and 2 ul of 1 uM Bumper (See table 3), and 1 ul of T7 DNA (0.5 ug), and water to 18 ul. The reactions are heated to 95 C. for 2 minutes. The reaction mixes were then cooled to 42 C. for 2 minutes at which time 1 ul (5 units) of Klenow polymerse along with 1 ul of mutant T7 polymerase were added. The reactions were incubated for 1 hour at 42 C.

When the reactions were complete, the tubes were spun briefly in the microfuge to collect any condensate on the tube caps. Then, 5 ul of each reaction was mixed with 2 ul of glycerol/bromphenol blue/xylene cyanol sample buffer. The reactions were then run on a 2% agarose gels in the presence of ethidium bromide. Products were visualized using short wave UV light.

Analysis of the results indicate that amplification products were obtained under the conditions outlined above. The reaction is dependent on the concentration of magnesium with the optimal amount of product obtained between 10 and 20 mM Magensium. Above this concentration, amplification is inhibited. In a separate set of experiments, complete reactions were prepared but without the addition of T7 template DNA. No products were obtained under these conditions. The reaction was also found to require 5 units of Klenow exo-polymerase and 100 units of the T7 mutant protein. These levels may be different as reaction conditions are optimized and improved.

What is claimed is:

1. A reaction mixture comprising
   i. a double stranded DNA comprising a target sequence flanked by a first and second end comprising a phage RNA polymerase recognition sequence on both the first and second ends wherein at least one end has a complementary sequence that forms a phage polymerase recognition site;
   ii. a first and second amplification primer each having a phage-encoded RNA polymerase recognition sequence wherein the first primer is complementary to the 5' end of the target sequence and the second primer is complementary to the antisense sequence of the 3' end of the target sequence;
   iii. phage-encoded RNA polymerase mutated to recognize and polymerize dNTP; and,
   iv. an excess of dNTP.

2. A reaction mixture of claim 1 wherein both ends of the DNA have phage polymerase recognition sites.

3. A reaction mixture of claim 1 wherein both ends of the DNA have identical phage polymerase recognition sites.

4. A reaction mixture of claim 1 wherein the DNA comprises a signature sequence for a specific genus or species of organism.

5. A reaction mixture of claim 1 wherein one end of the DNA has a complementary sequence that forms a phage polymerase recognition site.

* * * * *